United States Patent
Wong

(10) Patent No.: US 6,232,450 B1
(45) Date of Patent: May 15, 2001

(54) INHIBITION OF HUMAN FUCOSYLTRANSFERASES WITH N-LINKED LEWIS-X AND LACNAC ANALOGS

(75) Inventor: Chi-Huey Wong, Rancho Sante Fe, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/326,902

(22) Filed: Jun. 7, 1999

Related U.S. Application Data

(60) Provisional application No. 60/108,016, filed on Nov. 12, 1998.

(51) Int. Cl.$^7$ .......................... C07H 15/12; C07H 17/02; C07H 3/04; A61K 31/70
(52) U.S. Cl. .......................... 536/17.2; 514/61; 514/317; 514/326; 514/336; 514/352; 536/17.3; 536/17.4; 536/123.13; 546/207; 546/282.1; 546/283.1; 546/329
(58) Field of Search .............................. 514/61, 317, 326, 514/336, 352; 536/17.2, 17.3, 17.4, 123.13; 546/207, 282.1, 283.1, 329

(56) References Cited

U.S. PATENT DOCUMENTS 5,620,864 * 4/1997 Matta et al. ............................ 435/15

OTHER PUBLICATIONS

Wishnat et al., "Synthesis of a New Class of N–Linked Lewis and LacNAc Analogues as Potential Inhibitors of Human Fucosyltransferases . . . ", J. Org. Chem., vol. 63, No. 23, pp. 8361–8365, Oct. 1998.*
Beacham et al., "Inhibition of Fucosyl Transferase and Fucosidase by a Rigid Bicyclic Mimic of alpha–L–fucose", Tetrahedron Letters, vol. 39 (1–2): 151–154, Jan. 1998.*
Qiao et al., "Synergistic Inhibition of Human alpha–1, 3–Fucosyltransferase V", J. Amer. Chem. Soc., vol. 118, pp. 7653–7662, Aug. 1996.*
Hokke et al., "Identification of an alpha 3–fucosyltransferase and a novel alpha 2–fucosyltransferase activity in cercariae of the schistosome *Trichobilharzia ocellata* . . . ", Glycobiology, vol. 8(4): 393–406, 1998.*
Hanada et al., "The alpha 1—>3 fucosylation at the penultimate GlcNAc catalyzed by fucosyltransferase VII is blocked by internally fucosylated residue . . . ", Biochem. Biophys. Res. Commun., vol. 243(1): 199–204, 1998.*
Murray et al., "Mechanism and specificity of human alpha 1,3–fucosyltransferase V", Biochemistry, vol. 35(34): 11183–111995, Aug. 1996.*

Holmes, et al., "Biosynthesis of the Sialyl–Le$^x$ Determinant Carried by Type 2 Chain Glycosphingolipids (IV$^3$NeuAcIII$^3$FucnLc$_4$, VI$^3$Neu–AcV$^3$FucnLc$_6$, and VI$^3$NeuAcIII$^3$V$^3$Fuc$_2$nLc$_6$) in Human Lung Carcinoma PC9 cells", J. Biol. Chem. 261, 3737–3743 (1986).
Palcic, et al., "A Bisubstrate Analog Inhibitor for α(1→2)–Fucosyltransferase", J. Biol. Chem. 264: 17174–17181 (1989).
Luengo, et al., "Synthesis of C–Fucopyranosyl Analogs of GDP–L–Fucose as Inhibitors of Fucosyltransferases", Tet. Lett. 33: 6911–6914 (1992).
Wong, et al., "Specificity, Inhibition, and Synthetic Utility of a Recombinant Human α–1,3–Fucosyltransferase", J. Am. Chem. Soc. 114: 7321–73222 (1992).
Ichikawa, et al., "Chemical–Enzymatic Synthesis and Conformational Analysis of Sialyl Lewis x and Derivatives", J. Am. Chem. Soc. 114: 9283–9298 (1992).
Cai, et al., "Synthesis of Carbocyclic Analogues of Guanosine 5 '–(β–L–Fucopyranosyl diphosphate) (GDP–Fucose) as Potential Inhibitors of Fucosyltransferases", J. Org. Chem. 57: 6693–6696 (1992).
Natsuka, et al., "Enzymes Involved in Mammalian Oligosaccharide Biosynthesis", Curr. Opin. Struct. Biol. 4: 683–691 (1994).
Heskamp, et al., "Design and Synthesis of a Trisubstrate Analogue for α(1→3) Fucosyltransferase: A Potential Inhibitor", Tetrahedron 51: 8397–8406 (1995).
Heskamp, et al., "Expeditious Synthesis of a Trisubstrate Analogue for α(1→3 )Fucosyltransferase", J. Carbohydrate Chem. 14: 1265–1277 (1995).
Murray, et al., "Mechanism and Specificity of Human α–1, 3–Fucosyltransferase V", Biochem. 35: 11183–11195 (1996).
Qiao, et al., "Synergistic Inhibition of Human α–1,3–Fucosyltransferase V", J. Am. Chem. Soc. 118: 7653–7762 (1996).
Murray, et al., "Mechanism of Human α–1,3–Fucosyltransferase V: Glycosidic Cleavage Occurs Prior to Nucleophilic Attack", Biochem. 36: 823–831 (1997).

* cited by examiner

Primary Examiner—Howard C. Lee
(74) Attorney, Agent, or Firm—Donald G. Lewis

(57) ABSTRACT

A new class of N-linked Lewis and LacNAc analogs of are synthesized and shown to be effective inhibitors of human fucosyltransferases. In a high yielding reaction sequence the glucosamine derivative 1 was transformed to the 3-azido-2, 3-dideoxy sugar 2e under excellent stereocontrol. The LacNAc analog 4d was synthesized as a single isomer in three steps starting from 2e. In a one pot procedure iminocyclitol 5 was transformed into aldehyde 6 and successfully used for reductive amination with 4c and 2f yielding trisaccharide 8a, and disaccharide 7a.

5 Claims, 3 Drawing Sheets

2a X= OMs Y= H R¹ = R² = benzylidene
2b X= H Y= OH R¹ = R² = benzylidene
2c X= H Y= OMs R¹ = R² = benzylidene
2d X= H Y= OMs R¹ = Bn, R² = H
2e X= N₃ Y= H R¹ = Bn, R² = H
2f X= NH₂ Y= H R¹ = H, R² = H

INHIBITION OF HUMAN FUCOSYLTRANSFERASES WITH N-LINKED LEWIS-X AND LACNAC ANALOGS

This application claims the benefit of U.S. Provisional Application No. 60/108,016 filed on Nov. 12, 1998.

GOVERNMENT RIGHTS

This invention was made with government support under Grant No. CH 9310081 awarded by the National Science Foundation. The U.S. government has certain rights in the invention.

TECHNICAL FIELD

The present invention relates to fucosyltransferase inhibitors, including fucosyltransferase inhibitors having antiinflammatory and antitumor activity. In addition, the present invention relates to a method for synthesizing a new class of Lewis and LacNAc analogues having an iminocyclitol moiety linked through a 2 carbon spacer to a LacNAc mimetic and having inhibitory activity with respect to fucosyltransferases.

BACKGROUND

Many complex oligosaccharides on the cell surface are fucosylate (Varki, A. Glycobiology 1993, 3, 97–130; Hakomori et al. Adv. Cancer Res. 1989, 52, 257; Hakomori et al. J. Biol. Chem. 1984, 259, 4672; Feizi, T. Nature, 1985, 314, 53). These fucose containing structures are involved in cell-cell interactions which mediate inflammation, tumor development, and blood clotting (Ichikawa et al. 1994, Chem. Br. 117; Parekh et al. TIBTECH, 1994, 12, 339). The biosynthesis of these structures requires the action of several glycosyltransferases, of which fucosylation by a class of fucosyltransferases (FucT) is the last and critical step (Natsuka et al. Curr. Opin. Struct. Biol. 1994, 4, 683; Holme et al. J. Biol. Chem. 1986, 261, 3737; Kornfeld et al. Annu. Rev. Biochem. 1985, 54, 631–664). Therefore inhibitors of FucT are potentially useful as anti-inflammatory and anti-tumor drugs. To date only limited success has been achieved in the development of potent inhibitors of this important class of enzymes. Besides the production of unreactive analogs of GDP-fucose (Cai et al. J. Org. Chem. 1992, 57, 6693; Luengo et al. Tetrahedron Lett. 1992, 33, 6911) a bisubstrate inhibitor for α-1,2-fucosyltransferase has also been reported (Palcic et al. J. Biol. Chem. 1989, 264, 17174). Very recently, we and others have synthesized trisubstrate analogs, of α-1,3-fucosyltransferase (Heskamp et al. Tetrahedron, 1995, 51, 8397; Heskamp et al. J. Carbohydr. Chem. 1995, 14, 1265; Qiao et al. J. Am. Chem. Soc. 1996, 118, 7653). Although FucT V has been shown to have a catalytic residue with pKa=4.1, presumably an active site carboxylate, it has never been considered in the design of inhibitors until recently (Murray et al. Biochemistry, 1996, 34, 11183). Product inhibition studies with human α-1,3-fucosyltransferase (FucT V) have been used to establish that FucT V has an ordered, sequential, bi-bi mechanism with guanosine 5'-diphospho-β-1-fucose (GDP-Fuc) binding first and the product releasing last (Qiao et al. J. Am. Chem. Soc. 1996, 118, 7653; Murray et al. Biochemistry, 1997, 36, 823). Our past approach to the construction of fucosyltransferase inhibitors has been based on mimicking the proposed transition state by covalently linking an iminocyclitol to the 3-position of the acceptor substrate. Besides the fact the trisaccharide should form a complex with GDP and provide synergistic inhibition, it is assumed that a basic two carbon spacer could block the catalytic residue and improve the inhibition by additional hydrogen bonding (For synergistic inhibition see: (Wong et al. J. Am. Chem. Soc. 1992, 114, 7321; Ichikawa et al. J. Am. Chem. Soc. 1992, 114, 9283).

What is needed are improved fucosyltransferase inhibitors. Furthermore, what is needed is an efficient and general method for the synthesis of improved fucosyltransferase inhibitors.

SUMMARY OF THE INVENTION

The invention is directed to fucosyltransferase inhibitors and the synthesis of improved compounds. More particularly, the invention relates to an improved class of fucosyltransferase inhibitors Lewis and LacNAc analogues having an iminocyclitol moiety linked to an amino group of a LacNAc mimetic through a two carbon spacer moiety, as potential inhibitors of fucosyltransferases (FIG. 1; c).

One aspect of the invention is directed to a first type of fucosyltransferase inhibitor. This first type of fucosyltransferase inhibitor is represented by the following structure:

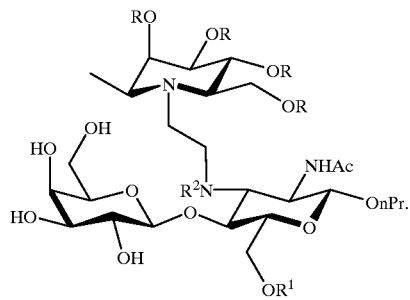

In the above structure, R and R$^1$ may be either hydrogen or benzyl. R$^2$ may be either hydrogen or methyl.

Another aspect of the invention is directed to a second type of fucosyltransferase inhibitor. This second type of fucosyltransferase inhibitor is represented by the following structure:

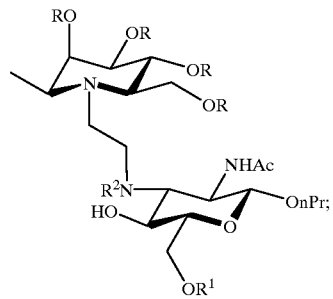

In the above structure, R and R$^1$ may be either hydrogen or benzyl. R$^2$ may be either hydrogen or methyl.

A further aspect of the invention is directed to processes for inhibiting a fucosyltransferase. In one mode of this aspect of the invention, the fucosyltransferase is inhibited by contact with a solution containing an inhibiting concentration of an inhibitor represented by the following structure:

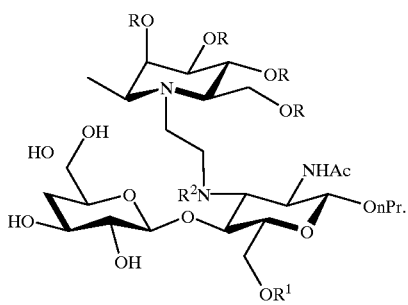

In a second mode of this aspect of the invention, the fucosyltransferase is inhibited by contact with a solution containing an inhibiting concentration of an inhibitor represented by the following structure:

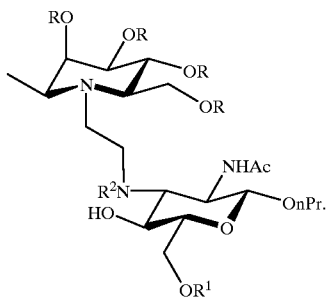

In both of the above structures, R and $R^1$ may be either hydrogen or benzyl; and $R^2$ may be either hydrogen or methyl.

Another aspect of the invention is directed to a process for synthesizing an inhibitor of fucosyltransferase represented by the following structure:

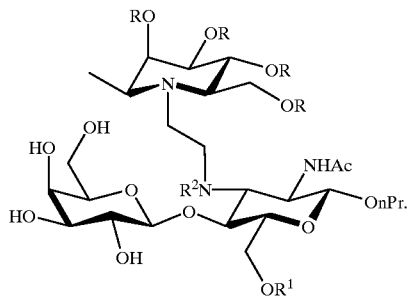

In the above structure, R and $R^1$ may be either hydrogen or benzyl; and $R^2$ may be either hydrogen or methyl. In the first step of this process, three reactants are admixed, i.e., an aldehyde, a disaccharaide, and $NaCNBH_3$ for producing a reductive amination intermediate. Preferred aldehydes are represented by the following structure:

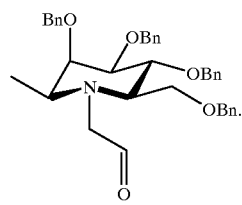

Preferred disaccharides are represented by the following structure:

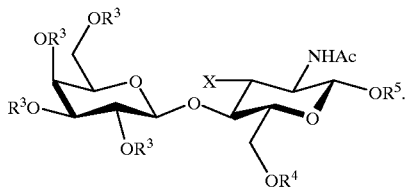

In the above disaccharide, $R^3$ may be either -benzoyl or —OH. $R^4$ may be either -benzyl or —OH. $R^5$ is n-propyl. X is —$NH_2$. Then the reductive amination intermediate is hydrogenated for producing said inhibitor of fucosyltransferase.

DETAILED DESCRIPTION OF THE INVENTION

Figure 1:
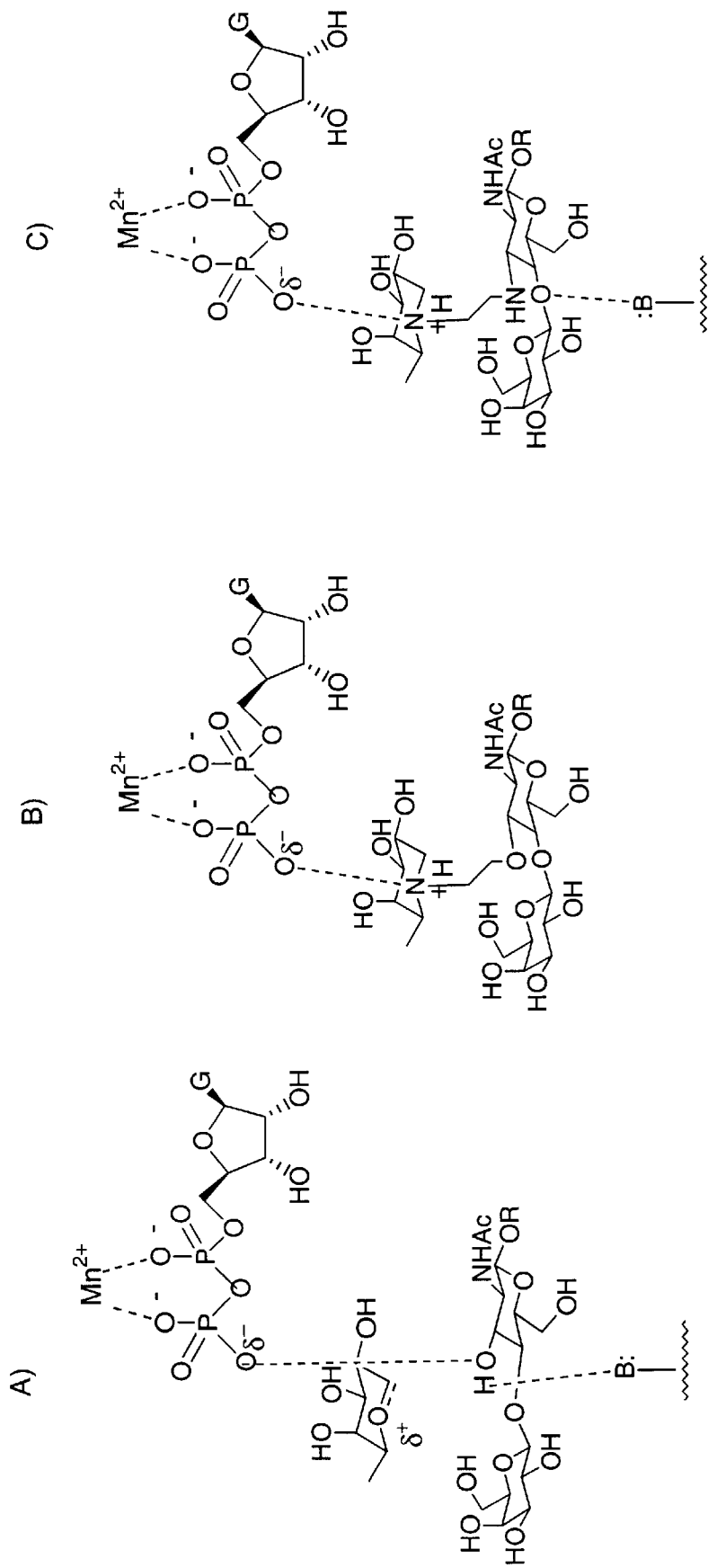
FIG. 1 illustrates the following: (a) proposed transition-state structure of the human α-1,3-fucosyltransferase reaction, (b) a synergistic inhibitor complex with GDP, (c) designed new inhibitor with an H-bonding interaction with the proposed base (a carboxylate group).

The invention relates to an improved class of fucosyltransferase inhibitors Lewis and and LacNAc analogues having an iminocyclitol moiety linked through a 2 carbon spacer to a LacNAc mimetic, as inhibitors of fucosyltransferases. (FIG. 1; c). The following examples contained herein, relate to the production of such compounds.

Synthesis of Intermediate Aminoglycoside 2f

Initially it appeared that oxidation of alcohol 1 (FIG. 2) to the corresponding ketone followed by reductive amination using allylamine should give an intermediate containing an appropriate spacer. This approach proved to be problematic under a variety of reaction conditions. Both oxidation and reductive amination of 1 proceed in low yield (15% overall); in addition, this methodology was unacceptable because it led almost exclusively to the undesired allo-configurated pyranose derivative. However, a successful route to the desired gluco isomer was then found which involves $S_N2$-type chemistry and provides excellent stereocontrol and high yields. Mesylate formation of 1 under standard conditions (FIG. 2) gave 2a (68%) which was reacted with NaOAc in 2-methoxy-ethanol to yield exclusively the allo-configurated alcohol 2b (Meyer zu Reckendorf, W. Chem. Ber. 1969, 102, 4207). Mesylation of 2b was accomplished in high yield (90%) leading to 2c. Reductive cleavage of the benzylidene using $NaCNBH_3$ and $HCl/Et_2O$ afforded mesylate 2d (70%) which was transformed using $NaN_3$ in DMF to the equatorial azide 2e as a single isomer (93%; Garegg et al. Carbohydr. Res. 1981, 93, C 10). The azido group not only activates the 4-OH for glycosylation, but it can also be used to attach the iminocyclitol moiety.

Figure 3:
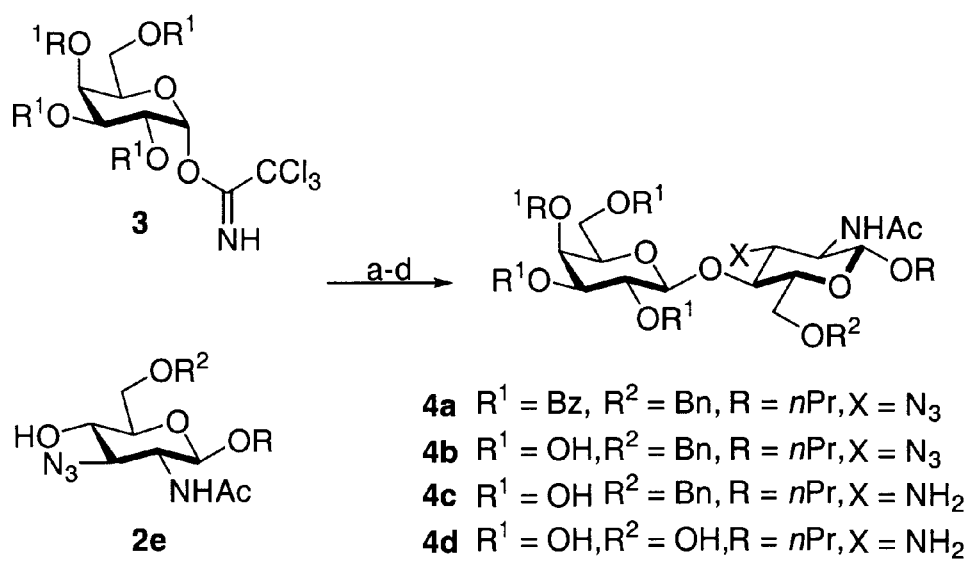
FIG. 3 illustrates the synthesis of compounds 4a, 4b, 4c, and 4d using the following steps: (a) $BF_3$/$CH_2Cl_2$, 0° C. to rt., 36 h, 70%; (b) $NaOCH_3$/MeOH, rt, 2 h, quant.; (c) P(OMe)$_3$, THF/$H_2O$, (10:1), NaOH, rt, 1 h, 81%; (d) HOAc/$H_2O$ (1:1), Pd(OH)$_2$/C-20%, Degussa-Type, 1 atm., $H_2$, 24 h, rt, quant.

Preparation of the LacNAc mimetic 4c (FIG. 3) involved a glycosylation step of alcohol 2e. The $BF_3 \cdot Et_2O$ promoted coupling of 2e using the known imidate 3 produced the desired disaccharide 4a as a single isomer (70%; Rio et al. Carbohydr. Res. 1991, 219, 71). Benzoate cleavage using $NaOCH_3/MeOH$ and Staudinger reduction (For a review on this subject see: Sriven et al. Chem. Rev. 1988, 88, 297 and references cited therein) of the crude product in $THF/H_2O$ using $P(OMe)_3$ afforded amine 4c in good yield over two steps (81%). Hydrogenolysis of 4c in $HOAc/H_2O$ using $Pd(OH)_2/C$, 20%-Degussa-Type and size exclusion chromatography provided the LacNAc mimetic 4d in quantitative yield (FIG. 3).

Figure 4:
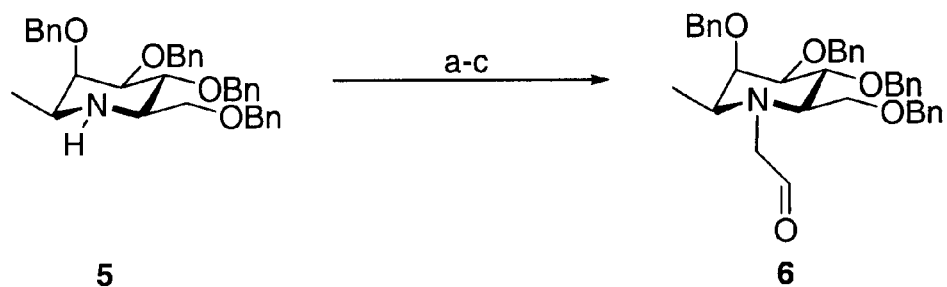
FIG. 4 illustrates the synthesis of compound 6: (a) methanesulfonicacid-trifluro-(2,2-dimethyl-1,3-dioxolan-4-yl)methylester, 0° C. to rt, 24 h, EtN(iPr)$_2$; (b) THF/3 M HCl, 60° C., 1 h; (c) NaIO$_4$, THF/$H_2O$, 0° C., 45 min., 52%, overall.

The convergent strategy for the synthesis of the Lewis x analog 8c (FIG. 5) involved a coupling of a C-2 functionalized iminocyclitol 5 with the LacNAc mimetic 4c. Because iminocyclitol 5 is known to have an unusually low pKa and nucleophilicity we assumed that only strong electrophiles could lead to N-alkylation (Hanozet et al. J. Biol. Chem. 1981, 256, 3703). In a one-pot procedure (FIG. 4) treatment of the readily available iminocyclitol 5 as described by us (Qiao et al J. Am. Chem. Soc. 1996, 118, 7653), with the triflate of isopropylidene-glycerol prepared in situ (Berkowitz et al. Tetrahedron, Lett. 1994, 35, 6445) gave, after acid induced cleavage of the acetal and $NaIO_4$ mediated oxidation of the diol intermediate, aldehyde 6 (52% overall) including only one purification step (FIG. 4).

Figure 5:
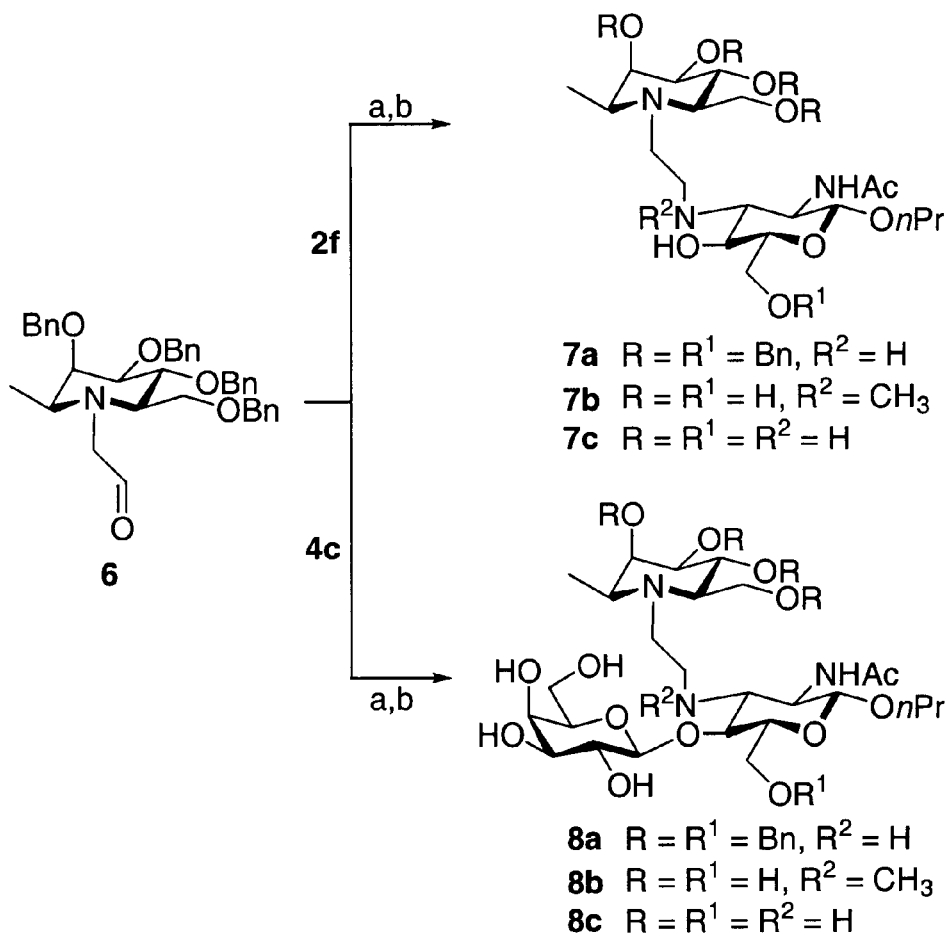
FIG. 5 illustrates the synthesis of inhibitors 7a, 7b, 7c, 8a, 8b, and 8c with the following reaction conditions: (a) $NaCNBH_3$, MeOH, rt, 6 h; (b) HOAc/$H_2O$, (1:1), Pd(OH)$_2$/C, 20%-Degussa-Type, 1 atm. $H_2$, then Bio-Gel P-2, 52% (8c), 57% (7c) overall.

Synthesis of N-Linked Lewis and LacNAc Inhibitors of Fucoysltransferase (FIG. 5)

Treatment of aldehyde 6 with amine 4c in a reductive amination sequence using $NaCNBH_3$ in MeOH afforded the desired trisaccharide 8c after hydrogenolysis (52% overall). The reductive amination of 6 with amine 2f leads to disaccharide 7c respectively (57% overall). It should be noted, that hydrogenolysis of the benzyl groups using Pd/C afforded mixtures of partially hydrogenated products under a variety of reaction conditions even at 60 psi. Interestingly when $Pd(OH)_2/C$, 20% Degussa-Type was used in MeOH, debenzylation was quantitative, however byproducts could be detected. Based on 1H NMR and HRMS 7b and 8b were formed as a result of reductive amination with formaldehyde which was probably generated in situ by PdII oxidation of MeOH (Choudary et al. Tetrahedron Lett. 1985, 26, 6257). However, when $HOAc/H_2O$ was used the hydrogenolysis of 7a and 8a proceeded cleanly and quantitatively.

In summary, the following example shows a short and effective synthesis of a new class of Lewis x and LacNAc analogs having inhitory activity with respect to fucosyltransferases. The method described represents a general procedure for the incorporation of an iminocyclitol as a transtition-state mimic of the sugar moiety of the donor to the acceptor substrate and may find use in the development of other glyscoyltransferase inhibitors.

While a preferred form of the invention has been shown in the drawings and described, since variations in the preferred form will be apparent to those skilled in the art, the invention should not be construed as limited to the specific form shown and described, but instead is as set forth in the claims.

Experimental Protocols

General: Anhydrous solvents were purchased from Aldrich and used without further purification. Cation exchange resin AG 50W-X2 ($H_+$ form, strongly acidic) was purchased from Bio-Rad Laboratories and converted to the appropriate salt form prior to its use. All reactions were run under dry Ar in oven-dried glassware, unless otherwise indicated. Analytical thin layer chromatography was performed using silica gel 60 $F_{254}$ precoated glass plates (Merck) and visualized by quenching of fluorescence and by charring after treatment with cerium molybdophosphate. Size exclusion chromatography was performed on Bio-Gel P-2 Gel, fine (Bio-Rad Laboratories). $_1H$ and $_{13}C$ NMR spectra were recorded at Bruker AMX 500 or Bruker AMX-400 and referenced to internal standard TMS to ($\delta_H$=0.00), $CDCl_3$ ($\delta_H$=7.26, $\delta_c$=77.0), $CD_3OD$ ($\delta_H$=4.87, $\delta_C$=49.2) or $D_2O$ ($\delta_H$=4.80).

Figure 2:
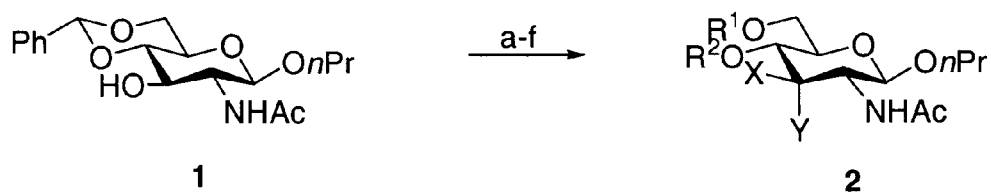
FIG. 2 illustrates the synthesis of compound 2 using the following steps: (a) MsCl/pyridine, 0° C., 24 h, 68%; (b) NaOAc, 2-methoxyethanol/$H_2O$, (95:5), reflux, 48 h, 80%; (c) MsCl/pyridine, 0° C. to rt, 24 h, 90%; (d) $NaCNBH_3$, HCl/$Et_2O$, rt, 6 h, 70%; (e) $NaN_3$/DMF, 80° C., 2 h, 93%; (f) HOAc/$H_2O$, (1:1), Pd(OH)$_2$/C-20%, Degussa-Type, 24 h, rt, , 1 atm., $H_2$, quant.

Synthesis of n-Propyl 2-Acetamido-3-O-mesyl-4,6-benzylidene-2-deoxy-β-D-glucopyra-noside (2a) as Shown in FIG. 2

Compound 1 (2.5 g, 7.12 mmol; Aldrich/Sigma) was dissolved in pyridine (40 mL), and cooled to 0° C. At this temperature (1.65 mL, 21.36 mmol) MsCl was added and stirring was continued for 24 h. All volatiles were removed in vacuo and the residue chromatographed with $CHCl_3/MeOH$ (100:1) to give 2a 2.1 g (68%). HRMS for $C_{19}H_{27}NO_8SNa$, (M+Na)+calcd 452.1355 found 452.1366.

Synthesis of n-Propyl 2-Acetamido-3-hydroxy-4,6-benzylidene-2-deoxy-β-D-allopyrano-side (2b) as Shown in FIG. 2

Mesylate 2a (2.0 g, 4.66 mmol) was suspended in a mixture of methoxyethanol/$H_2O$ (30 mL, 95:5) and NaOAc (3.8 g, 46.30 mmol) was added and the resulting mixture heated to reflux for 48 h, cooled to rt. and evaporated to dryness. The residue was dissolved in 30 mL $H_2O$, and the water layer was extracted with $CHCl_3$ (3×100 mL) dried over $MgSO_4$ and concentrated. Flash chromatography ($CHCl_3/MeOH$, 20:1) gave the title compound 1.32 g (80%) as a white solid. HRMS for $C_{18}H_{25}NO_6$, (M+H)+calcd 352.1760 found 352.1752.

Synthesis of n-Propyl 2-Acetamido-3-O-mesyl-4,6-benzylidene-2-deoxy-β-D-allopyrano-side (2c) as Shown in FIG. 2

Starting from 2b (1.32 g, 3.76 mmol) following the procedure described for the synthesis of 2a, with the exception that the mixture was allowed to warm up to rt., afforded the title compound 1.45 g (90%) as a white solid. HRMS for $C_{19}H_{27}NO_8Cs$, $(M+Cs)_+$ calcd 562.0512 found 562.0492.

Synthesis of n-Propyl 2-Acetamido-3-O-mesyl-4-hydroxy-6-O-benzyl-2-deoxy-β-D-allo-pyranoside (2d) as Shown in FIG. 2

At rt. acetal 2c (1.04 g, 2.42 mmol) was dissolved in THF (50 mL) and 12 g MS 3 Å was added followed by $NaCNBH_3$ (46.6 mL of a 1 M solution in THF) and HCl in $Et_2O$ (20 mL of a 1 M solution). The resulting mixture was stirred at rt. for additional 6 h, diluted with $CHCl_3$ (300 mL) and $H_2O$ (100 mL). The organic layer was separated, dried over $MgSO_4$ and concentrated. The residue was purified by flash chromatography using $CHCl_3$/MeOH (20:1) to gave the title compound 730 mg (70%) as a white solid. HRMS for $C_{19}H_{29}NO_8S$, $(M+H)_+$ calcd 432.1692 found 432.1669.

Syntheis of n-Propyl 2-Acetamido-3-azido-4-hydroxy-6-O-benzyl-2,3-dideoxy-β-D-allo pyranoside (2e) as Shown in FIG. 2

Mesylate 2d (380 mg, 0.88 mmol) was dissolved in dry DMF (15 mL) and $NaN_3$ (860 mg, 13.2 mmol) was added. The resulting mixture was heated to 80° C. for 2 h, cooled to rt. and evaporated to dryness. The residue was purified by flash chromatography using $CHCl_3$/MeOH (20:1) to give the title compound 310 mg (93%). HRMS for $C_{11}H_{22}N_2O_5$, $(M+H)_+$ calcd 263.1607 found 263.1613.

Synthesis of n-Propyl 2-N-Acetamido-3-azido-6-O-benzyl-2,3-dideoxy-4-O-(2,3,4,6-tet-ra-O-benzoyl-β-D-galactopyranosyl)-β-D-glucopyranoside (4a) as Shown in FIG. 3

At 0° C. $BF_3$ (25 μL, 0.2 mmol) was added dropwise to a solution of alcohol 2e (250 mg, 0.66 mmol) and imidate 3 (1.22 g, 1.64 mmol) in dry $CH_2Cl_2$ (8 mL). The mixture was allowed to warm up to rt. and stirred for an additional 6 h. Then another portion of $BF_3$ (25 μL, 0.2 mmol) and imidate 3 (540 mg, 0.73 mmol) was added and stirring continued for additional 30 h. Then $NEt_3$ (100 μL, 0.70 mmol) and 15 mL toluene were added and the mixture evaporated to dryness in vacuum and the residue purified by flash chromatography using Hexane/EtOAc (1:1) to give the title compound 442 mg (70%). HRMS for $C_{52}H_{52}N_4O_{14}Cs$, $(M+Cs)_+$ calcd 1089.2534 found 1089.2565.

Synthesis of n-Propyl 2-N-Acetamido-3-amino-6-O-benzyl-2,3-dideoxy-β-D-galactopy-ranosyl-β-D-glucopyranoside (4c) as Shown in FIG. 3

Disaccharide 4a (270 mg, 0.28 mmol) was dissolved in dry MeOH (5 mL) and $NaOCH_3$ (30 μL of a 0.5 M solution in MeOH) was added. The resulting mixture was stirred for 2 h and neutralized with cation exchange resign AG 50W-X2 ($H_+$ form) and concentrated. The residue was dissolved in THF/$H_2O$ (14 mL, 10:1) and NaOH (15 μL of a 1 M aq. solution) was added followed by $P(OMe)_3$ (283 μL of a 1 M solution in THF) the mixture was stirred at rt. for 1 h concentrated and purified by flash chromatography using ($CH_2Cl_2$/MeOH, 5:1 containing 3% $NEt_3$) to give the title compound as a white solid 117 mg (81%) over two steps. HRMS for $C_{24}H_{38}N_2O_{10}CS$, $(M+Cs)_+$ calcd 647.1581 found 647.1603.

Synthesis of n-Propyl 2-N-Acetamido-3-amino-2,3-dideoxy-β-D-galactopyranosyl-β-D-glucopyranoside (4d) as Shown in FIG. 3

Disaccharide 4c (19 mg, 40 μmol) was dissolved in HOAc/$H_2O$ (1:1, 2 mL and Pd(OH)$_2$/C-20%-Degussa-Type was added and $H_2$ introduced by two evaporations in vacuo. The mixture was stirred at rt. for 24 h, filtered over a thin pad of Celite and concentrated in vacuum, size exclusion chromatography using Bio-Gel P-2 gave 4d, after lyophylization, as a white solid, 10.8 mg (100%). HRMS for $C_{17}H_{32}N_2O_{10}$, $(M+H)_+$ calcd 425.2135 found 425.2147.

Synthesis of 1,3,4,5-Tetra-O-benzyl-2,6-(N-2-oxoethyl-imino)-2,6,7-trideoxy-L-glycero-D-manno-heptitol (6) as Illustrated in FIG. 4

At 0° C. amine 5 (240 mg, 0.45 mmol; Aldrich/Sigma) was dissolved in dry $CH_2Cl_2$ (5 mL) and $EtN(iPr)_2$ (100 μL, 0.57 mmol) was added followed by the triflate of isopropylideneglycerol$_{15}$ (1.18 g, 4.5 mmol). The resulting mixture was stirred at 0° C. for 10 min. and additional 24 h at rt., diluted with $CH_2Cl_2$ (30 mL) and washed with saturated $NaHCO_3$ (3×20 mL). The organic layer was dried over $MgSO_4$ and concentrated in vacuum. The oil observed above was dissolved in THF/3 M HCl (8 mL, 1:1) and heated to 60° C. for 1 h, cooled to rt. and the pH was adjusted to 8.5 using $NaHCO_3$. The mixture was extracted with EtOAc (3×20 mL), the organic layer dried over $MgSO_4$ and concentrated to give a white solid. The solid was dissolved in THF (6 mL) and cooled to 0° C., and $NaIO_4$ (96 mg, 0.45 mmol) dissolved in water (6 mL) was added at one portion and the resulting mixture stirred at 0° C. for 45 min. Then EtOAc (50 mL) was added and the organic layer washed with saturated $Na_2S_2O_3$ dried over $MgSO_4$ and concentrated in vacuum. Flash chromatography using Hexan/EtOAc (2:1) gave 6 (Rf=0.3) as a colorless oil 135 mg (52%, overall). HFMS for $C_{37}H_{41}NO_5$, $(M+Cs)_+$ calcd 712.2039 found 712.2009.

Synthesis of n-Propyl 2-N-Acetamido-2,3-dideoxy-(β-D-galactopyranosyl)-6-O-benzyl-3amino-(2-(N-(1,3,4,5-tetra-O-benzyl-β-L-homofuconojirimycinyl))amino-ethyl-β-D-glucopyranoside (8a) as Shown in FIG. 5

Aldehyde 6 (10.8 mg, 18.6 μmol; See FIG. 4 description and above for synthesis of this simple intermediate) and disaccharide 4c (7.8 mg, 15.1 μmol) were dissolved in dry MeOH (1.5 mL) and $NaCNBH_3$ (7.82 mg, 124 μmol) was added. The mixture was stirred at rt. until TLC ($CH_2Cl_2$/MeOH, 10:1) showed the disappearance of the disaccharide and the formation of a new product (Rf=0.1). The mixture was evaporated to dryness and purified by flash chromatography using ($CH_2Cl_2$/MeOH, 10:1) to gave the title compound as a glassy solid 8.5 mg (52%). HRMS for $C_{61}H_{79}N_3O_{14}$, $(M+H)_+$ calcd 1078.5640 found 1078.5723.

Synthesis of n-Propyl 2-N-Acetamido-2,3-dideoxy-6-O-benzyl-3-amino-(2-(N-(1,3,4,5-tetra-O-benzyl-β-L-homofuconojirimycinyl))aminoethyl-β-D-glucopyranoside (7a) as Illustrated in FIG. 5

Following the procedure described for the synthesis of 8a aldehyde 6 (25 mg, 43 μmol) and monosaccharide 2f (10.5 mg, 30 μmol), gave the title compound as a white solid 14.2 mg (57%). HRMS for $C_{55}H_{69}N_3O_9Cs$, $(M+Cs)_+$ calcd 1048.4088 found 1048.4072.

Synthesis of n-Propyl 2-N-Acetamido-2,3-dideoxy-4-O-(β-D-galactopyranosyl)-3-amino-(2-(N-(β-L-homofuconojirimycinyl))aminoethyl-β-D-glucopyranoside (8c) as illustrated in FIG. 5

Hydrogenolysis of 8a (8.3 mg, 7.7 μmol) following the procedure described for the synthesis of 4d gave the title compound as a glassy solid 4.8 mg (100%). HRMS for $C_{26}H_{49}N_3O_{14}CS$, $(M+Cs)_+$ calcd 760.2269 found 760.2244.

Synthesis of n-Propyl 2-N-Acetamido-2,3-dideoxy-3-amino-(2-(N-(β-L-homofuconojirimycinyl))aminoethyl-β-D-glucopyranoside (7c) as Illustrated in FIG. 5

Hydrogenolysis of 7a (14.1 mg, 15.3 μmol) following the procedure described for the synthesis of 4d gave the title compound as a glassy solid 7.0 mg (100%). HRMS for $C_{20}H_{39}N_3O_9$, $(M+H)_+$ calcd 466.2766 found 466.2776.

General Fucosyl Transferase Assay: Inhibition of Fucosyl Transferase by Inhibitors 7a, 7b, 7c, 8a, 8b, or 8c GDP-Fuc concentration was varied (10, 25, 50, 100 mM) at fixed concentrations of inhibitor (7a, 7b, 7c, 8a, 8b, or 8c) (0, 20, 40, 80 mM), and the acceptor sugar, LacNAc-b-O-(CH$_2$)$_5$CO$_2$CH$_3$, was kept at twice its $K_m$ level, 0.6 mM. Each assay contained 0.3 munit of FucT V and 10 mM MnCl$_2$ in a 100 mM MES buffer (pH 6.0). Reactions were 30 minutes at room temperature. The precise $K_i$ was determined with a nonlinear, least squares fit of the data to the equation for competitive inhibition.

General evidence that inhibitor (7a, 7b, 7c, 8a, 8b, or 8c) (0, 20, 40, 80 mM) was not a slow substrate or an inactivator was obtained. A 0.350 mL solution that contained 10 mM MnCl2, 2.1 munits FucT V, 0.30 mM LacNAc-b-O-(CH$_2$)$_5$CO$_2$CH$_3$, 0.010 mM inhibitor (7a, 7b, 7c, 8a, 8b, or 8c), and 100 mM MES (pH 6.0). This solution was subject to incubation at room temperature for various time periods (0, 3, 10, 20, 30, 60, 80 min). After the incubation time, a 0.050 mL aliquot was removed and GDP-[U-$^{14}$C]-fucose was added to a final concentration of 0.050 mM to initiate the fucosyltransfer reaction. After a 30 minute reaction time period, the solution was passed through a Dowex 1 column and the amount of product determined. A control reaction was performed that did not contain (7a, 7b, 7c, 8a, 8b, or 8c) inhibitor which was used in the calculation of percent inhibition.

Fluorometric Assay for α-1,3-Fucosyltransferase V Activity

The fluorometric assay monitored GDP production using the pyruvate kinase/lactate dehydrogenase coupled enzymatic assay for the consumption of NADH based on an assay for GTPase activity (Gonzalo et al., 1995). NADH fluorescence has an excitation wavelength of 340 nm and an emission wavelength of 460 nm. All solutions were filtered through a 0.22 mm filter. A 0.460 mL 100 mM MES (pH 7.7) coupling enzyme buffer contained the coupling substrates and cofactors (0.032 mM NADH, 0.50 mM PEP, 2 mM MnCl$_2$). The assay reactions were individually incubated in the fluorimeter at 37° C. until a flat baseline was achieved. The coupled enzymatic reactions were initiated with the addition of 0.040 mL of a coupling enzymes solution that contained 69 units of rabbit muscle pyruvate kinase and 27 units of rabbit muscle lactate dehydrogenase. A standard curve of the change in absorbance at 460 nm was prepared with 0.5, 1.0, 2.0, 4.0, and 8.0 mM GDP and had the following for typical results 0.64, 1.42, 2.57, 4.40, 8.69. A value of 1.3 absorbance units were observed per 1.0 mM of GDP. These results correlated with the change in emission at 460 nm predicted by multiplying the ratio of the GDP and NADH concentrations to the total initial fluorescence at 460 nm.

A time course of the fucosyltransferase reaction was determined. A 0.700 mL reaction containing 0.05 mM inhibitor (7a, 7b, 7c, 8a, 8b, or 8c) in lieu of GDP-Fuc, 0.60 mM LacNAc-b-O—(CH$_2$)$_5$CO$_2$CH$_3$, 10 mM MnCl$_2$, and 75.6 munits of FucT V. At the following time points, 0.100 mL aliquots were taken: 5, 10, 30, 45, 90, 130 min. The reactions were quenched with the addition of 0.460 mL of coupled enzymatic assay buffer (100 mM MES, pH 7.7) that contained the required amounts of PEP, NADH and MnCl$_2$. After equilibration of the sample at 37° C., a 0.040 mL solution of pyruvate kinase and lactate dehydrogenase was added. The change in emission at 460 nm that occurred in 20 s was measured. The time course was linear to the 45 minutes. Initial rate data was subsequently taken after 30 minutes of reaction.

What is claimed is:

1. A fucosyltransferase inhibitor represented by the following structure:

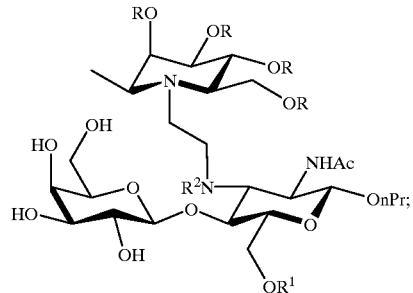

wherein R is selected from the group consisting of hydrogen and benzyl; R$^1$ is selected from the group consisting of hydrogen and benzyl; and R$^2$ is selected from the group consisting of hydrogen and methyl.

2. A fucosyltransferase inhibitor represented by the following structure:

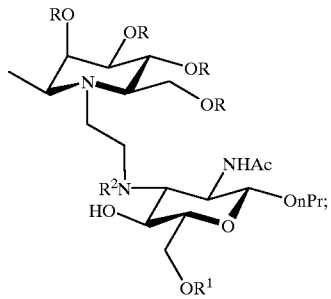

wherein R is selected from the group consisting of hydrogen and benzyl; R$^1$ is selected from the group consisting of hydrogen and benzyl; and R$^2$ is selected from the group consisting of hydrogen and methyl.

3. A process for inhibiting α-1,3-fucosyltransferase V comprising the following step:

contacting the α-1,3-fucosyltransferase V with a solution containing an inhibiting concentration of an inhibitor represented by the following structure:

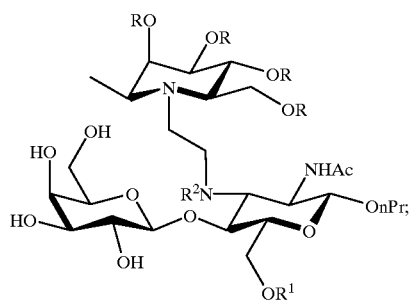

wherein R is selected from the group consisting of hydrogen and benzyl; $R^1$ is selected from the group consisting of hydrogen and benzyl; and $R^2$ is selected from the group consisting of hydrogen and methyl.

4. A process for inhibiting α-1,3-fucosyltransferase V comprising the following step:

contacting the α-1,3-fucosyltransferase V with a solution containing an inhibiting concentration of an inhibitor represented by the following structure:

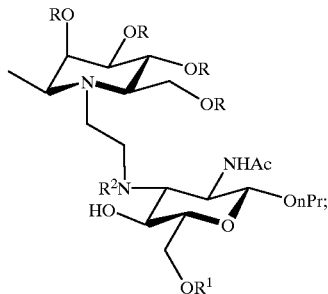

wherein R is selected from the group consisting of hydrogen and benzyl; $R^1$ is selected from the group consisting of hydrogen and benzyl; and $R^2$ is selected from the group consisting of hydrogen and methyl.

5. A process for synthesizing an inhibitor of fucosyltransferase represented by the following structure:

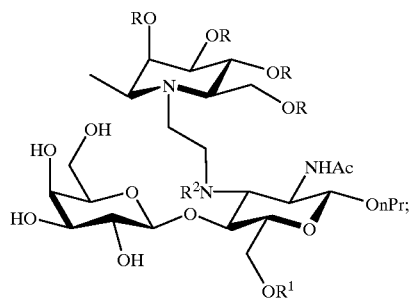

wherein R is selected from the group consisting of hydrogen and benzyl; $R^1$ is selected from the group consisting of hydrogen and benzyl; and $R^2$ is selected from the group consisting of hydrogen and methyl, said process comprising the following steps:

Step A: admixing an aldehyde represented by the following structure:

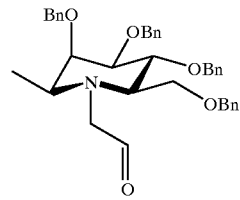

with a disaccharide represented by the following structure:

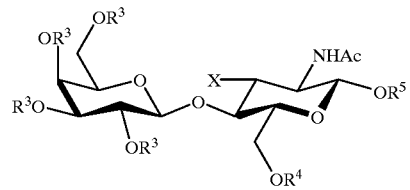

wherein: $R^3$ is a radical selected from the group consisting of -benzoyl, and —OH; $R^4$ is a radical selected from the group consisting of -benzyl and —OH; $R^5$ is n-propyl; and X is —$NH_2$;

and with $NaCNBH_3$ for producing a reductive amination intermediate; and then

Step B: hydrogenating the reductive amination intermediate of said Step A for producing said inhibitor of fucosyltransferase.

* * * * *